United States Patent [19]

Sakashita et al.

[11] Patent Number: 4,548,689

[45] Date of Patent: Oct. 22, 1985

[54] PHOTOCURABLE RESIN COMPOSITION

[75] Inventors: Takeshi Sakashita, Iwakuni; Takayuki Nakano, Otake, both of Japan

[73] Assignee: Mitsui Petrochemical Industries, Ltd., Tokyo, Japan

[21] Appl. No.: 654,243

[22] Filed: Sep. 25, 1984

[30] Foreign Application Priority Data

Sep. 28, 1983 [JP] Japan .................. 58-178109
May 29, 1984 [JP] Japan .................. 59-107512
May 29, 1984 [JP] Japan .................. 59-107513

[51] Int. Cl.$^4$ .......................... C08F 2/50; A61K 5/00
[52] U.S. Cl. ........................... 204/159.23; 523/115; 523/116
[58] Field of Search ............. 204/159.23; 523/115, 523/116

[56] References Cited

U.S. PATENT DOCUMENTS

| | | | |
|---|---|---|---|
| 4,038,350 | 7/1977 | Jaques | 204/159.20 |
| 4,129,667 | 12/1978 | Lorenz et al. | 204/159.23 |
| 4,134,811 | 1/1979 | Poortere et al. | 204/159.18 |
| 4,165,265 | 8/1979 | Nakabayashi et al. | 204/159.19 |
| 4,264,483 | 4/1981 | Laufer et al. | 204/159.23 |
| 4,323,348 | 4/1982 | Schmitz-Josten et al. | 524/854 |
| 4,439,380 | 3/1984 | Michl et al. | 204/159.23 |

FOREIGN PATENT DOCUMENTS

| | | |
|---|---|---|
| 79-10986 | 5/1979 | Japan . |
| 80-33687 | 9/1980 | Japan . |
| 81-120610 | 9/1981 | Japan . |
| 82-54107 | 3/1982 | Japan . |
| 82-120506 | 7/1982 | Japan . |

*Primary Examiner*—Herbert J. Lilling
*Attorney, Agent, or Firm*—Wenderoth, Lind & Ponack

[57] ABSTRACT

Disclosed is a photocurable composition comprising (a) a radical-polymerizable monomer, (b) an α-ketocarbonyl compound and (c) a derivative of mercaptobenzimidazole, mercaptobenzothiazole or mercaptobenzoxazole or an aromatic amine nucleus-substituted with an electron-attractive group. This composition has a high photocuring speed at a temperature close to normal temperature and gives a cured product excellent in various physical properties. This composition is valuable as a dental adhesive or resin.

13 Claims, No Drawings

PHOTOCURABLE RESIN COMPOSITION

BACKGROUND OF THE INVENTION (1) Field of the Invention

The present invention relates to a photocurable resin composition which is excellent in the photo-curability at low temperatures close to normal temperature and provides a cured product excellent in the adhesion characteristics such as the water-resistant adhesion strength and also in the hardness, strength and color tone. More particularly, the present invention relates to a photocurable resin composition which shows excellent properties as a curable composition for teeth, such as a tooth adhesive, a tooth composite resin or a tooth rigid resin.

(2) Description of the Prior Art

Various curable compositions comprising a radical-polymerizable monomer such as a (meth)acrylic acid ester type vinyl monomer and a polymerization initiator have been proposed as curable compositions for teeth, such as tooth adhesives, composite resins and rigid resins.

A tooth adhesive is required to have a high curing speed at low temperatures close to normal temperature and to provide a cured product excellent in the adhesion strength to teeth and the water-resistant adhesion strength. A tooth composite resin or tooth rigid resin is required to have a curability at low temperatures close to normal temperature and to provide a cured product which is excellent not only in the above-mentioned adhesion characteristics but also in the mechanical properties such as strength, compression strength, hardness and abrasion resistance and the color tone. With recent rapid progress of the tooth-repairing curative technique, the above-mentioned properties required for curable compositions for teeth become severe.

In connection with conventional curable compositions for teeth comprising a radical-polymerizable monomer such as a (meth)acrylic acid ester type vinyl monomer and a polymerization initiator, there have been proposed several methods in which a photopolymerization initiator is used as the polymerization initiator and photocuring is effected, whereby the above-mentioned properties are improved. For example, Japanese Patent Publications No. 10986/79 and No. 33687/78 propose a process in which polymerization is carried out in the presence of a photopolymerization initiator comprising a carbonyl compound such as α-diketone and an amine.

Even if this known combination of a carbonyl compound and an amine is used for photocuring a radical-polymerizable monomer of the (meth)acrylic acid ester type having an aromatic polycarboxylic acid or its anhydride structure and the cured product is applied to the above-mentioned uses of the photocurable resin composition for teeth, no satisfactory results can be obtained because the cured product is inferior in the color tone and water-resistant adhesion strength.

Recently, Japanese Patent Application Laid-Open Specification No. 5407/82 and DE-OS 3,029,276 teach that when a 2-cyanoethylamine, especially N-methyl-N-cyanoethylamine, is used as the amine promoter for the photopolymerizable composition, the curing-promoting action is enhanced and there can be attained effects of preventing coloration of the cured resin and eliminating the amine smell.

We previously found that when a composition comprising a radical-polymerizable monomer including 4-methacryloyloxyethoxycarbonylphthalic acid or its anhydride and a vinyl compound and a free radical generator is used as a tooth adhesive, a cured product excellent in the adhesion characteristics such as the adhesion strength and water-resistant adhesion strength is obtained, and we proposed this photocurable composition in Japanese Patent Application Laid-Open Specification No. 12338/79 and Japanese Patent Publication No. 17513/83.

This photocurable composition for teeth is excellent in the adhesion characteristics, mechanical properties and color tone but is still insufficient in the curing speed.

SUMMARY OF THE INVENTION

In view of the above-mentioned conventional curable compositions for teeth and the properties required for these compositions, we made research with a view to ddveloping a photocurable composition excellent in the curing characteristics and capable of providing a cured product excellent in the adhesion characteristics, mechanical properties and color tone. As the result, it was found that this object can be attained by photocuring a composition comprising a radical-polymerizable monomer, an α-ketocarbonyl compound and a specific aromatic amine by irradiation with light. We have now completed the present invention based on this finding.

The photocurable composition of the present invention has a high photocuring speed at low temperatures close to normal temperature and is excellent in the adhesion characteristics such as the adhesion strength and water-resistant adhesion strength and this composition provides a cured product excellent in the color tone and the mechanical properties such as strength, compression strength, hardness and abrasion resistance. Accordingly, this photocurable composition has properties required for a curable composition for teeth, such as a tooth adhesive, a composite resin or a rigid resin and is suitable for tooth treatments. Furthermore, the photocurable composition of the present invention can be used as an adhesive at the precision processing step, a metal adhesive or a composite resin in various fields. Moreover, if the present invention is applied to photopolymerization of the above-mentioned radical-polymerizable monomer of the (meth)acrylic acid ester type having an aromatic polycarboxylic acid or its anhydride structure instead of a known ordinary radical-polymerizable monomer, the above-mentioned excellent effects are further enhanced.

In accordance with the fundamental aspect of the present invention, there is provided a photocurable composition comprising (a) a radical-polymerizable monomer, (b) an α-ketocarbonyl compound and (c) an amine, wherein the amine (c) is at least one member selected from the group consisting of compounds represented by the following general formula:

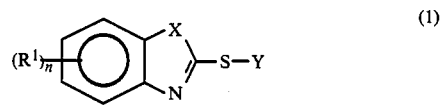

(1)

wherein X stands for $>NR^2$, an oxygen atom or a sulfur atom, Y stands for a hydrogen atom, $-SR^3$ or a monovalent, divalent or trivalent metal, $R^1$ stands for an alkyl group, an aryl group, an aralkyl group or a halogen atom, n is an integer of from 0 to 4 with the proviso that when n is 2 or larger, a plurality of groups $R^1$ may be the same or different, $R^2$ stands for a hydrogen atom, an alkyl group, an aryl group or an aralkyl group, and R³ stands for an alkyl group or an aryl group, or a group represented by the following general formula:

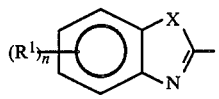 (2)

wherein X, R¹ and n are as defined above, and substituted amines represented by the following general formula:

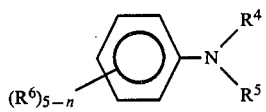 (3)

wherein R⁴ stands for a hydrogen atom or an alkyl group, R⁵ stands for a hydrogen atom, an alkyl group, a hydroxyalkyl group or an aryl group, R⁶ stands for a monovalent, electron-attractive atom or organic group, and n is an integer of from 0 to 4.

DETAILED DESCRIPTION OF THE PREFERRED EMBODIMENTS

The radical-polymerizable monomer (a) used for the photocurable composition of the present invention is an ordinary radical-polymerizable monomer having a carbon-to-carbon unsaturation. More specifically, the monomer (a) includes an unsaturated carboxylic acid monomer, an ester type unsaturated monomer, a nitride type unsaturated monomer and an aromatic vinyl compound. As the unsaturated carboxylic acid monomer, there can be mentioned acrylic acid and methacrylic acid. As the ester type unsaturated monomer, there can be mentioned ordinary (meth)acrylic acid ester type monomers and unsaturated esters of lower aliphatic carboxylic acids such as vinyl acetate and allyl acetate. As the nitrile type unsaturated monomer, there can be mentioned acrylonitrile and methacrylonitrile. As the aromatic vinyl compound, there can be mentioned styrene, α-methylstyrene, vinyltoluene and isopropenyltoluene.

Specifically, the (meth)acrylic acid ester type monomer is a (meth)acrylic acid ester type compound formed from acrylic acid or methacrylic acid and a monohydroxyl or polyhydroxyl compound. More specifically, there can be mentioned alkyl (meth)acrylates such as methyl(meth)acrylate and ethyl(meth)acrylate, and 2-hydroxyethyl(meth)acrylate, 2-hydroxypropyl(meth)acrylate, ethylene glycol di(meth)acrylate, propylene glycol di(meth)acrylate, triethylene glycol di(meth)acrylate, polyethylene glycol di(meth)acrylate, butylene glycol di(meth)acrylate, hexylene glycol di(meth)acrylate, 2,2-bis[4-(meth)acryloyloxyphenyl]propane, 1,3-di(meth)acryloyloxyethoxybenzene, 2,2-bis[4-(meth)acryloyloxycyclohexyl]propane, 2,2-bis[3-(meth)acryloyloxy-2-hydroxypropoxyphenyl]propane, trimethylol propane tri(meth)acrylate, pentaerythritol tetra(meth)acrylate and dipentaerythritol hexa(meth)acrylate.

As another compound belonging to the (meth)acrylic acid ester type monomer, there can be mentioned an aromatic polycarboxylic acid or its anhydride having at least one (meth)acryloyloxyl group in the molecule. The (meth)acryloyloxyl group-containing aromatic polycarboxylic acid or its anhydride is a compound having an ester structure formed by reacting at least one hydroxyl group of an alkane polyol or polyoxyalkane polyol having at least two hydroxyl groups in the molecule with one carboxyl group of an aromatic polycarboxylic acid having at least three carboxyl groups in the molecule.

As the alkane polyol having at least two hydroxyl groups in the molecule, which constitutes the (meth)acryloyloxyl group-containing aromatic polycarboxylic acid (a), there can be mentioned ethylene glycol, 1,2-propylene glycol, 1,3-propylene glycol, butylene glycol, trimethylol propane, glycerol and pentaerythritol. As the polyoxyalkane polyol having at least two hydroxyl groups in the molecule, there can be mentioned diethylene glycol, triethylene glycol, tetraethylene glycol, dipropylene glycol, dibutylene glycol, ditrimethylol propane, diglycerol, triglycerol and dipentaerythritol, and compounds represented by the following formulae:

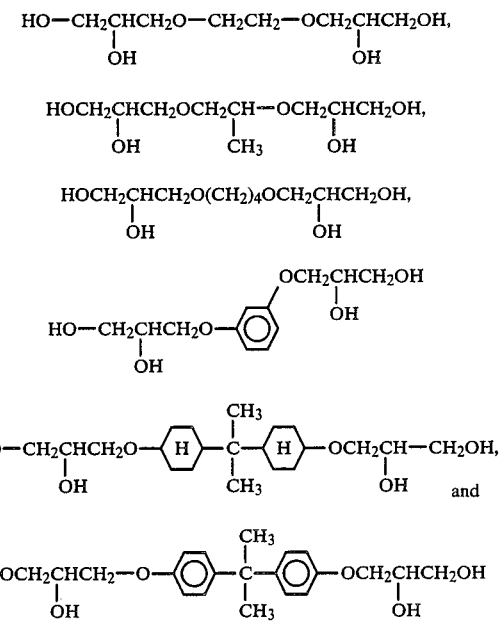

As the (meth)acrylic acid component constituting the (meth)acryloyloxyl group-containing aromatic polycarboxylic acid, there can be mentioned acrylic acid and methacrylic acid. An aromatic polycarboxylic acid in which at least two carboxyl groups are bonded to adjacent carbon atoms on the aromatic nucleus is preferred as the aromatic polycarboxylic acid component having at least three carboxyl groups. More specifically, there can be mentioned hemimellitic acid, trimellitic acid, prehnitic acid, mellophanic acid and pyromellitic acid.

As the (meth)acryloyloxyl group-containing aromatic polycarboxylic acid or its anhydride, there can be mentioned 4-(meth)acryloyloxymethoxycarbonyl phthalic acid or its anhydride, 4-(meth)acryloyloxyethoxycarbonylphthalic acid or its anhydride, 4-[2-hydroxy-3-(meth)acryloyloxypropoxycarbonyl]phthalic acid or its anhydride, 2,3-bis(3,4-dicarboxybenzoyloxy)propyl(meth)acrylate or its anhydride and 2-(3,4-dicarboxy)propane or its anhydride, and compounds represented by the following formulae:

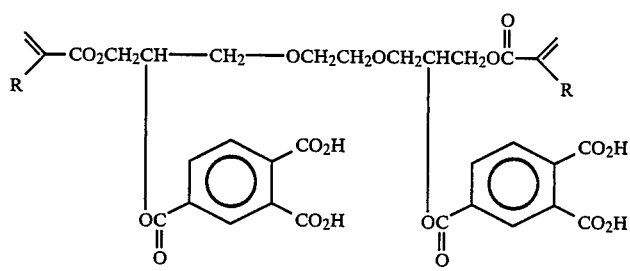
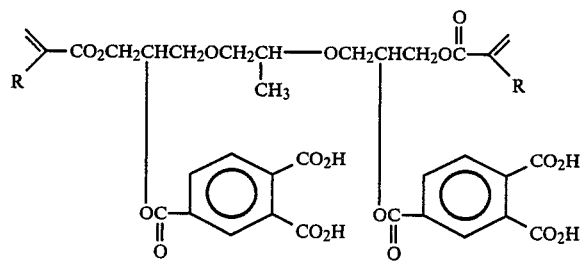
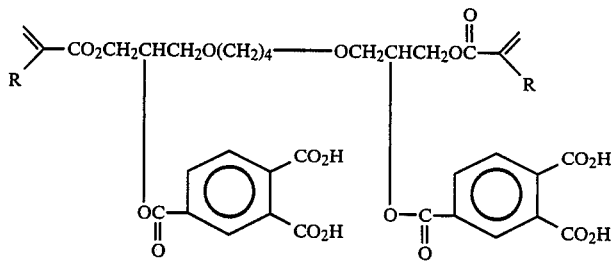
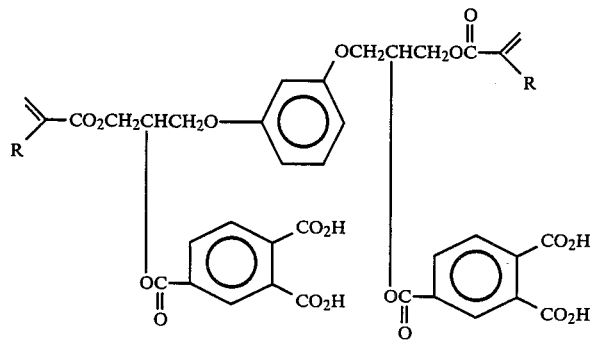
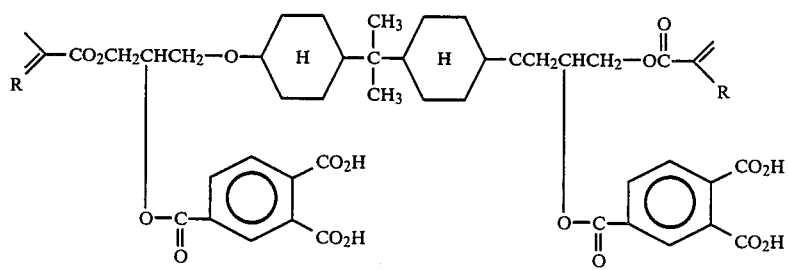

-continued

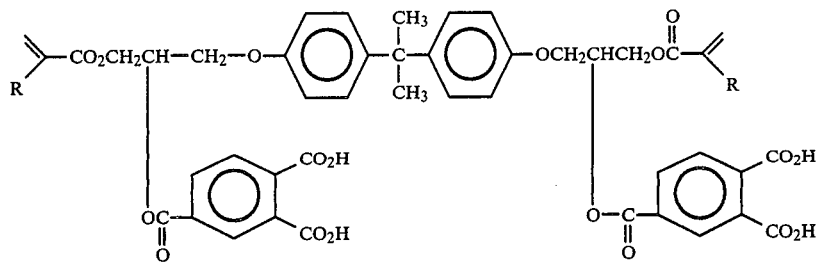

wherein R stands for a hydrogen atom or a methyl group, or acid anhydrides of these compounds. Among the above-exemplified compounds, 4-(meth)acryloyloxyethoxycarbonylphthalic acid or its anhydride is preferred, and 4-(meth)acryloyloxyethoxycarbonylphthalic anhydride is especially preferred.

The foregoing radical-polymerizable monomers may be used singly or in the form of mixtures of two or more of them. However, when the photocurable composition of the present invention is used as a dental resin composition, there is preferably used a monomer mixture comprising (i) an ester monomer of an aliphatic alcohol or aliphatic polyol with methacrylic acid and (ii) at least one monomer selected from the group consisting of an ester of a polyol having a bisphenol skeleton or dihydric phenol skeleton with methacrylic acid and a methacryloxyl group-containing aromatic polycarboxylic acid or its anhydride. The monomers (i) and (ii) may be used at a (i)/(ii) weight ratio of from 5/95 to 95/5.

The photopolymerization initiator to be incorporated into the photocurable composition of the present invention consists of an α-ketocarbonyl compound (b) and an amine (c).

The α-ketocarbonyl compound includes an α-diketone, an α-ketoaldehyde, an α-ketocarboxylic acid and an α-ketocarboxylic acid ester. More specifically, there can be mentioned α-diketones such as diacetyl, 2,3-pentadione, 2,3-hexadione, benzil, 4,4'-dimethoxybenzil, 4,4'-diethoxybenzil, 4,4'-oxybenzil, 4,4'-dichlorobenzil, 4-nitrobenzil, α-naphthil, β-naphthil, camphorquinone and 1,2-cyclohexanedione, α-ketoaldehydes such as methylglyoxal and phenylglyoxal, and pyruvic acid, benzoylformic acid, phenylpyruvic acid, methyl pyruvate, ethyl benzoylformate, methyl phenylpyruvate and butyl phenylpyruvate. Among these α-ketocarbonyl compounds, α-diketones are preferably used from the viewpoint of the stability or the like. Among α-diketones, diacetyl, benzil and camphorquinone are preferred, and camphorquinone is especially preferred.

In the composition of the present invention, an amine selected from specific amines described below is used as the amine.

As the amine of the first group, there can be mentioned aromatic compounds represented by the following general formula (1):

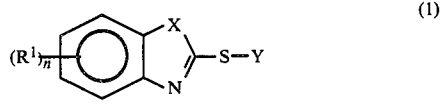
(1)

wherein X stands for >NR$^2$, an oxygen atom or a sulfur atom, Y stands for a hydrogen atom, —SR$^3$ or a monovalent, divalent or trivalent metal, the number of the residue

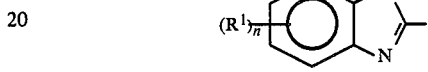

is 1 or the same as the valency number of the metal when Y is a divalent or trivalent metal, R$^1$ stands for an alkyl, aryl or aralkyl group ordinarily having 1 to 20 carbon atoms, or a halogen atom, n is an integer of from 0 to 4, with the proviso that when n is 2 or larger, a plurality of the groups R$^1$ may be the same or different, R$^2$ stands for a hydrogen atom, an alkyl, aryl or aralkyl group ordinarily having 1 to 20 carbon atoms, and R$^3$ stands for an alkyl group or an aryl group, or a group represented by the following general formula (2):

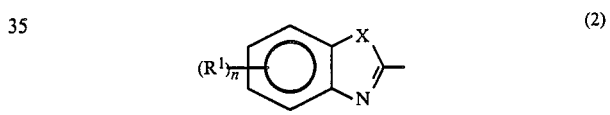
(2)

wherein X, R$^1$ and n are as defined above.

As specific examples of R$^1$ in the above-mentioned aromatic sulfur compound of the formula (1), there can be mentioned a hydrogen atom, alkyl groups ordinarily having 1 to 6 carbon atoms, such as methyl, ethyl, propyl, butyl, pentyl and hexyl groups, aryl groups ordinarily having 6 to 20 carbon atoms, such as phenyl, tolyl, xylyl, cumyl and naphthyl groups, aralkyl groups ordinarily having 7 to 20 carbon atoms, such as benzyl, phenylethyl, phenylisopropyl, naphthylmethyl and naphthylethyl groups, and halogen atoms such as fluorine, chlorine, bromine and iodine. As specific examples of R$^2$, there can be mentioned a hydrogen atom and alkyl, aryl and aralkyl groups exemplified above as R$^1$. As specific examples of R$^3$, there can be mentioned alkyl and aryl groups exemplified above as R$^1$. As specific examples of the group represented by the general formula (2), there can be mentioned a benzimidazole group, a benzoxazole group, a benzothiazole group, a methylbenzimidazole group, a methylbenzoxazole group and a methylbenzothiazole group. As specific examples or Y, there can be mentioned a hydrogen atom, metals of the group Ia such as lithium, sodium and potassium, metals of the group Ib such as copper and silver, metals of the group IIa such as magnesium, calcium, strontium and barium, metals of the group IIb such as zinc, cadmium and mercury, metals of the group III such as alminum, gallium and yttrium, and metals of the groups VIb, VIIb and VIII such as chromium, molybdenum, manganese, iron, cobalt, nickel, ruthenium, rhodium and palladium.

As specific examples of the aromatic compound (c) represented by the general formula (2), there can be mentioned 2-mercaptobenzimidazole, 2-mercaptobenzoxazole, 2-mercaptobenzothiazole, 2-mercaptomethylbenzimidazole, 2-mercaptomethylbenzoxazole, 2-mercaptomethylbenzothiazole, dibenzooxazyl disulfide, dibenzothiazyl disulfide, 2-(phenylthio)benzothiazole, sodium 2-mercaptobenzimidazole, zinc (II) 2-mercaptobenzimidezole, copper (II) 2-mercaptobenzimidazole, nickel (II) 2-mercaptobenzimidazole, zinc (II) 2-mercaptobenzothiazole, copper (II) 2-mercaptobenzotiazole, zinc (II) 2-mercaptomethylbenzimidazole, zinc (II) 2-mercaptomethylbenzothiazole, 2-mercaptodimethylbenzimidazole, 2-mercaptodimethylbenzoxazole, 2-mercaptodimethylbenzothiazole and 2-mercaptotetramethylbenzothiazole. Among these sulfur compounds, there are preferably used 2-mercaptobenzimidazole, 2-mercaptobenzoxazole, 2-mercaptobenzothiazole, 2-mercaptomethylbenzothiazole, dibenzothiazyl disulfide, zinc (II) 2-mercaptobenzimidazole, zinc (II) 2-mercaptobenzothiazole and zinc (II) 2-mercaptomethylbenzothiazole, and 2-mercaptobenzothiazole, 2-mercaptomethylbenzothiazole, zinc (II) 2-mercaptobenzothiazole and zinc (II) 2-mercaptomethylbenzothiazole.

These amines are prominently characterized in that they contain a mercapto group (—S—) in addition to the nitrogen atom contained in the 5-membered ring. These amines are advantageous over the known amines in that the curing speed at low temperatures is high and it provides a cured product having no substantial discoloration and a good water resistance.

Amines of another group used in the photocurable composition of the present invention are nucleus-substituted amines represented by the following general formula (3):

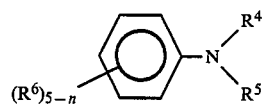

In the above general formula (3), $R^4$ stands for a hydrogen atom or an alkyl group ordinarily having 1 to 6 carbon atoms, such as a methyl, ethyl, propyl, butyl, pentyl or hexyl group. $R^5$ stands for a hydrogen atom, an alkyl group having 1 to 6 carbon atoms, such as mentioned above, a hydroxyalkyl group such as a hydroxymethyl, 2-hydroxyethyl, 2-hydroxypropyl, hydroxybutyl, hydroxypentyl or hydroxyhexyl group, or an aryl group such as a phenyl, tolyl, ethylphenyl, propylphenyl, isopropylphenyl, dimethylphenyl, fluorophenyl, chlorophenyl, dichlorophenyl, bromophenyl, methoxyphenyl, ethoxyphenyl, isopropoxyphenyl, dimethoxyphenyl, nitrophenyl or dinitrophenyl group. $R^6$ stands for a monovalent, electron-attractive atom or organic group, and it is especially preferred that $R^6$ be a group represented by the following general formula (4):

wherein $R^7$ stands for a hydrogen atom or an alkyl, hydroxyalkyl or aryl group as exemplified above with respect to $R^5$, or a hydroxyl group, an alkoxyl group ordinarily having 1 to 6 carbon atoms, such as a methoxyl, ethoxyl, propoxyl or butoxyl group, or an amino group of the formula —$NR^8R^9$ in which $R^8R^9$ stand for a hydrogen atom or an alkyl group having 1 to 4 carbon atoms, such as exemplified above with respect to $R^4$.

An aniline derivative substituted by an electron-attractive group, especially a group represented by the general formula (4), is excellent over an analogous aniline derivative free of such a substituent in the curing speed at room temperature and provides a cured product having no discoloration and improved physical properties.

As the above-mentioned substituted aromatic amine, there can be mentioned 4-dimethylaminobenzaldehyde, 4-diethylaminobenzaldehyde, 4-(methylhexylamino)-benzaldehyde, 4-(methylphenylamino)benzaldehyde, 4-(β-hydroxyethylmethylamino)benzaldehyde, 4-dimethylaminobenzoic acid, 4-diethylaminobenzoic acid, 4-(methylhexylamino)benzoic acid, 4-(β-hydroxyethylmethylamino)benzoic acid, methyl 4-dimethylaminobenzoate, methyl 4-diethylaminobenzoate, methyl 4-dipropylaminobenzoate, methyl 4-(methylhexylamino)benzoate, methyl 4-(methylphenylamino)benzoate, propyl 4-(β-hydroxyethylmethylamino)benzoate, hexyl 4-dimethylaminobenzoate, phenyl 4-dimethylaminobenzoate, 4-dimethylaminophthalic acid, 4-dimethylaminoisophthalic acid and dimethyl 4-dimethylaminoisophthalate. Among these substituted aromatic amines, 4-dimethylaminobenzaldehyde, 4-dimethylaminobenzoic acid and methyl 4-dimethylaminobenzoate are preferred.

As the electron-attractive group other than those represented by the general formula (4), there can be mentioned a cyano group, a nitro group and a halogen atom in the order of importance. The aromatic amine of this type is slightly inferior to an amine having a substituent represented by the general formula (4) in the curing speed. However, an aniline derivative nucleus-substituted with a cyano group is superior to an aniline derivative having an alkyl chain substituted with a cyano group in the curing speed at normal temperature. As specific examples of the aromatic amine of this type, there can be mentioned N,N-dimethyl-o-cyanoaniline, N,N-dimethyl-o-nitroaniline, N,N-dimethyl-o-chloroaniline, N,N-dimethyl-o-bromoaniline, N,N-dimethyl-o-iodoaniline, N,N-dimethyl-m-cyanoaniline, N,N-dimethyl-m-nitroaniline, N,N-dimethyl-m-chloroaniline, N,N-dimethyl-m-nitroaniline, N,N-dimethyl-m-chloroaniline, N,N-dimethyl-m-bromoaniline, N,N-dimethyl-p-cyanoaniline, N,N-dimethyl-p-nitroaniline, N,N-dimethyl-p-chloroaniline, N,N-dimethyl-p-bromoaniline, N,N-diethyl-o-cyanoaniline, N,N-diethyl-m-cyanoaniline, N,N-diethyl-p-cyanoaniline, N,N-diethyl-p-chloroaniline, N,N-dipropyl-p-cyanoaniline, N,N-dibutyl-p-cyanoaniline, N,N-methylphenyl-p-cyanoaniline, N,N-β-hydroxyethylmethyl-p-chloroaniline, N,N-dimethyl-2,4-dicyanoaniline, N,N-dimethyl-2,4-dinitroaniline and N,N-dimethyl-2,4-dichloroaniline. Among these substituted aromatic amines, N,N-dimethyl-p-cyanoaniline and N,N-diethyl-p-cyanoaniline are preferred.

It should be understood that in the composition of the present invention, the α-diketone, α-ketoaldehyde, α-ketocarboxylic acid or substituted amine may be present in the form bonded to the side chain or terminal of the polymer.

In the photocurable composition of the present invention, the α-ketocarbonyl compound is incorporated in an amount of 0.01 to 15 parts by weight, preferably 0.05 to 10 parts by weight, per 100 parts by weight of the radical-polymerizable monomer and the substituted aromatic amine is incorporated in an amount of 0.01 to 15 parts by weight, preferably 0.05 to 10 parts by weight, per 100 parts by weight of the radical-polymerizable monomer. The molar ratio of the substituted aromatic amine to the α-ketocarbonyl compound is ordinarily in the range of from 0.1 to 10, preferably in the range of from 0.2 to 5.

If necessary, the photocurable composition of the present invention may further comprise other components such as a powdery inorganic filler, an organic polymer, a tackifier, a photosensitizer, a polymerization modifier and a polymerization inhibitor. As the powdery inorganic filler, there can be mentioned, for example, kaolin, talc, clay, calcium carbonate, silica, silica-alumina, alumina, titanium oxide, calcium phosphate, glass powder and quartz powder. As the organic polymer, there can be mentioned a wax, an ethylene-vinyl acetate copolymer polymethyl methacrylate and polymethyl acrylate. These components may be incorporated in optional amounts.

When the photocurable composition of the present invention is irradiated with light, polymerization is caused to cure the composition. Both the natural rays and artificial rays may be used as the light, and rays of the ultraviolet and visible regions can be adopted. For production of artifical rays, there may be used a high pressure mercury lamp, a medium pressure mercury lamp, a low pressure mercury lamp, a halogen lamp and a tungsten lamp. The temperature adopted for the photocuring reaction is ordinarily 0° to 80° C., preferably 5° to 50° C., and irradiation is ordinarily conducted for 1 second to 5 minutes.

The present invention will now be described in detail with reference to the following examples that by no means limit the scope of the invention.

EXAMPLE 1

A mixture comprising 70 g of triethylene glycol dimethacrylate, 25 g of 2,2-bis[4-(3-methacryloyloxypropoxy)phenyl]propane, 5 g of 4-methacryloyloxyethoxycarbonylphthalic anhydride and 50 g of finely divided silica (Aerosil R-972 supplied by Nippon Aerosil K.K.) was kneaded at room temperature by two rolls to form a composition. On one surface of a polypropylene plate having a thickness of 3 mm and a circular through hole having a diameter of 3 mm was placed another polypropylene plate, and 2 g of the above composition, 5 mg of camphorquinone and 5 mg of 4-dimethylaminobenzaldehyde were sufficiently mixed by a spatula and the resulting photocurable composition was packed into the circular hole. Visible rays (having a wavelength of 350 to 700 nm) were applied by using a visible ray irradiator (Translux supplied by Kulzer Co.) set 1 cm above the photocurable composition. The curing time and the color tone of the cured product were examined. The curing time was expressed by the shortest visible ray irradiation time necessary for reducing the penetration (under a load of 1 kg) to zero on the surface of the cured product opposite to the visible ray-irradiated surface. The obtained results are shown in Table 1.

EXAMPLES 2 THROUGH 23 AND COMPARATIVE EXAMPLES 1 THROUGH 5

Photocurable compositions were prepared in the same manner as described in Example 1 except that compounds shown in Table 1 were used in amounts shown in Table 1 as the α-ketocarbonyl compound and substituted aromatic amine instead of camphorquinone and 4-dimethylaminobenzaldehyde used in Example 1, and the curing times and color tones of these compositions were examined in the same manner as described in Example 1. The obtained results are shown in Table 1.

TABLE 1

| Example No. | α-Ketocarbonyl Compound (amount, mg) | Amine (amount, mg) | Curing time (seconds) | Color Tone of Cured Product |
|---|---|---|---|---|
| 1 | camphorquinone (5) | 4-dimethylaminobenzaldehyde (5) | 25 | colorless |
| 2 | camphorquinone (5) | 4-dimethylaminobenzoic acid | 30 | " |
| 3 | camphorquinone (5) | methyl 4-dimethylaminobenzoate (5) | 20 | " |
| 4 | benzil (5) | methyl 4-dimethylaminobenzoate (5) | 35 | " |
| 5 | diacetyl (5) | methyl 4-dimethylaminobenzoate (5) | 25 | " |
| 6 | camphorquinone (5) | 4-dimethylaminobenzaldehyde (10) | 20 | " |
| 7 | camphorquinone (20) | methyl 4-dimethylaminobenzoate (10) | 15 | " |
| 8 | camphorquinone (5) | 2-mercaptobenzimidazole (5) | 15 | " |
| 9 | camphorquinone (5) | 2-mercaptobenzothiazole (5) | 30 | " |
| 10 | camphorquinone (5) | 2-mercaptobenzoxazole (5) | 35 | " |
| 11 | camphorquinone (5) | 2-mercaptomethylbenzothiazole (5) | 30 | " |
| 12 | camphorquinone (5) | zinc (II) 2-mercaptomethylbenzothiazole (5) | 30 | " |
| 13 | camphorquinone (5) | zinc (II) 2-mercaptomethylbenzooxazole (5) | 35 | " |
| 14 | benzil (5) | 2-mercaptobenzothiazole (5) | 35 | " |
| 15 | diacetyl (5) | 2-mercaptobenzothiazole (5) | 35 | " |
| 16 | camphorquinone (10) | 2-mercaptobenzothiazole (10) | 25 | " |
| 17 | camphorquinone (20) | 2-mercaptobenzothiazole (10) | 20 | " |
| 18 | camphorquinone (5) | N,N—dimethyl-p-cyanoaniline (5) | 30 | " |
| 19 | camphorquinone (5) | N,N—diethyl-p-cyanoaniline (5) | 30 | " |
| 20 | benzil (5) | N,N—dimethyl-p-cyanoaniline (5) | 35 | " |

TABLE 1-continued

| Example No. | α-Ketocarbonyl Compound (amount, mg) | Amine (amount, mg) | Curing time (seconds) | Color Tone of Cured Product |
| --- | --- | --- | --- | --- |
| 21 | diacetyl (10) | N,N—dimethyl-p-cyanoaniline (10) | 35 | " |
| 22 | camphorquinone (20) | N,N—dimethyl-p-cyanoaniline (15) | 25 | " |
| 23 | camphorquinone (20) | N,N—dimethyl-p-cyanoaniline (20) | 20 | " |
| Comparative Example 1 | camphorquinone (5) | tri-n-hexylamine (5) | >180 | " |
| Comparative Example 2 | camphorquinone (5) | N,N—dimethylaniline (5) | 40 | yellow |
| Comparative Example 3 | camphorquinone (5) | N—methyl-N—2-cyanoethylaniline (5) | 40 | " |
| Comparative Example 4 | camphorquinone (5) | N—methyl-N—2-chloroethyl-aniline (5) | 45 | light yellow |
| Comparative Example 5 | camphorquinone (5) | N—methyl-N—2-cyanoethyl-p-nitroaniline (5) | 45 | light yellow |

EXAMPLE 24

A photocurable liner was prepared by adding 30 mg of camphorquinone and 30 mg of methyl 4-dimethylaminobenzoate to 3 g of a primer composition comprising 93 parts by weight of methyl methacrylate. 5 parts by weight of 2,2-bis[4-(3-methacryloyloxy-2-hydroxypropoxy)phenyl]propane and 2 parts byweight of 4-methacryloyloxyethoxycarbonylphthalic anhydride. A hole having a diameter of 3 mm and a depth of 2 mm was formed in a bovine anterior tooth lip and etching was carried out for 45 seconds with a 65% aqueous solution of phosphoric acid, followed by water washing and drying. The above-mentioned liner was thinly coated on the circular hole of the bovine tooth. Than a photocurable composition formed by sufficiently mixing by a spatula 7 g of triethylene glycol dimethacrylate, 2.5 g of 2,2-bis[4-(3-methacryloyloxy-2-hydroxypropoxy)phenyl]propane, 5 g of finely divided silica (Aerosil R-972 supplied by Nippon Aerosil K.K.), 40 mg of camphorquinone and 40 mg of methyl 4-dimethylaminobenzoate was filled in the liner-treated circular hole of the bovine tooth, and visible rays were applied for 2 minutes to cure the photocurable composition.

The sample was immersed in water overnight, and in order to examine the filled state, the sample was immersed in cold water at 4° C. and warm water at 60° C. alternately at intervals of 1 minute 60 times as a whole for a total immersion time of 2 hours. Then, removal of the filled substance by a pincette was tried, but it was impossible to remove the filled substance from the dentine.

COMPARATIVE EXAMPLE 6

A photocurable liner and a photocurable composition were prepared in the same manner as in Example 24 except that 4-methacryloyloxyethoxycarbonylphthalic anhydride was not incorporated in the photocurable liner and 40 mg of N,N-dimethylaniline was used for the photocurable composition instead of 40 mg of methyl 4-dimethylaminobenzoate, and the filling operation was carried out on a bovine tooth in the same manner as described in Example 24. In the same manner as described in Example 24, the sample was immersed in water and subjected to the heat cycle test. When removal of the filled substance by a pincette was tried, the filled substance was easily peeled from the dentine.

EXAMPLE 25

A photocurable liner was prepared in the same manner as described in Example 24 except that 2-mercaptobenzothiazole was used instead of methyl 4-dimethylaminobenzoate, and a circular hole of a bovine tooth was treated with this liner in the same manner as described in Example 24. A photocurable composition formed by sufficiently mixing by a spatula 5 g of triethylene glycol dimethacrylate, 5 g of 2,2-bis[4-(3-methacryloyloxy-2-hydroxypropoxy)phenyl]propane, 10 g of finely divided silica (Aerosil RM-50 supplied by Nippon Aerosil K.K.), 40 mg of camphorquinone and 40 mg of 2-mercaptobenzothiazole was filled in the liner-treated circular hole of the bovine tooth, and irradiation with visible rays was conducted for 30 seconds to cure the photocurable composition.

The sample was immersed in water overnight, and in order to examine the filled state, the sample was immersed in cold water at 4° C. and warm water at 60° C. alternately at intervals of 1 minute 60 times as a whole for a total immersion time of 2 hours. When removal of the filled substance by a pincette was tried, the filled substance was not peeled from the dentine.

EXAMPLE 26

The experiment was carried out in the same manner as described in Example 25 except that N,N-dimethyl-p-cyanoaniline was used instead of 2-mercaptobenzothiazole. Results similar to those obtained in Example 25 were obtained.

EXAMPLE 27

A bovine tooth hole was treated with the same liner as used in Example 24, and a photocurable composition formed by sufficiently mixing by a spatula 5 g of triethylene glycol, 5 g of 1,3-dimethacryloyloxyethoxybenzene, 10 g of finely divided silica (Aerosil RM50 supplied by Nippon Aerosil K.K.), 30 mg of camphorquinone and 30 mg of methyl 4-dimethylaminobenzoate was filled in the liner-treated tooth hole. Irradiation with visible rays was conducted for 30 seconds to cure the photocurable composition. The immersion test was carried out in the same manner as described in Example 24. Results similar to those obtained in Example 24 were obtained.

EXAMPLE 28

The enamel of the lip surface of a bovine anterior tooth was sufficiently polished with emery paper No. 6/0 to smooth the surface. The tooth was etched for 45 seconds with a 65% aqueous solution of phosphoric acid, followed by sufficient washing with water. The etched surface was dried by air and a cellophane tape (about 13 mm × about 13 mm) having a circular hole having a diameter of 5.4 mm was applied to the etched surface. The same photocurable liner as described in Example 24 was finely coated in the circular hole, and after standing at room temperature for 2 minutes, irradiation with visible rays was conducted for 2 minutes. Two compositions were prepared by sufficiently kneading 1% by weight of benzoyl peroxide or 0.6% by weight of dimethyl-p-toluidine into a kneaded composition comprising 50 parts by weight of triethylene glycol dimethacrylate, 25 parts by weight neopentyl glycol dimethacrylate, 25 parts by weight of 2,2-bis[4-(3-methacryloyloxy-2-hydroxypropoxy)phenyl]propane and 20 parts by weight of finely divided silica. Equal amounts of the two compositions containing benzoyl peroxide and dimethyl-p-toluidine, respectively, were mixed and kneaded sufficiently with each other. By using the so-prepared adhesive composition, an acrylic resin rod having a diameter of 5 mm was butt-bonded to the linear-treated enamel surface of the bovine tooth. The bonded structure was allowed to stand still overnight. The bonded sample was immersed in cold water at 4° C. and warm water at 60° C. alternately at intervals of 1 minute 60 times as a whole for a total immersion time of 2 hours. Then, the sample was allowed to stand in air maintained at 23° C. for 10 minutes, and the bonding forth between the bovine tooth and the acrylic resin rod was measured at 23° C. at a pulling speed of 2 mm/min. It was found that the bonding force was 131 Kg/cm$^2$.

The bonding test was carried out in the same manner as described above by using the photocurable liners used in Examples 25 and 26, and it was found that the bonding forces were 120 Kg/cm$^2$ and 121 Kg/cm$^2$, respectively.

COMPARATIVE EXAMPLE 7

A bonded test piece was prepared in the same manner as described in Example 28 except that a curable liner formed by adding 30 mg of camphorquinone and 30 mg of dimethylaniline to 3 g of a composition comprising 95 parts by weight of methyl methacrylate and 5 parts by weight of 2,2-bis[4-methacryloyloxy-2-hydroxypropoxy)phenyl]propane was used instead of the photocurable liner used in Example 28, and the bonding force between the bovine tooth and the acrylic resin rod was measured in the same manner as described in Example 28. It was found that the bonding force was 32 Kg/cm$^2$.

We claim:

1. A photocurable composition comprising (a) a radical-polymerizable monomer, (b) an α-ketocarbonyl compound and (c) an amine, wherein the amine (c) is at least one member selected from the group consisting of compounds represented by the following general formula:

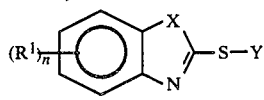

wherein X stands for >NR$^2$, an oxygen atom or a sulfur atom, Y stands for a hydrogen atom, —SR$^3$ or a monovalent, divalent or trivalent metal, R$^1$ stands for an alkyl group, an aryl group, an aralkyl group or a halogen atom, n is an integer of from 0 to 4 with the proviso that when n is 2 or larger, a plurality of groups R$^1$ may be the same or different, R$^2$ stands for a hydrogen atom, an alkyl group, an aryl group or an aralkyl group, and R$^3$ stands for an alkyl group or an aryl group, or a group represented by the following general formula:

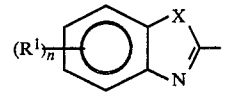

wherein X, R$^1$ and n are as defined above, and substituted amines represented by the following general formula:

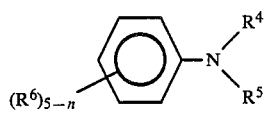

wherein R$^4$ stands for a hydrogen atom or an alkyl group, R$^5$ stands for a hydrogen atom, an alkyl group, a hydroxyalkyl group of an aryl group, R$^6$ stands for a monovalent, electron-attractive atom or organic group, and n is an integer of from 0 to 4.

2. A composition as set forth in claim 1, wherein the amine (c) is 2-mercaptobenzothiazole, 2-mercaptomethylbenzothiazole, zinc (II) 2-mercaptobenzothiazole or zinc (II) 2-mercaptomethylbenzothiazole.

3. A composition as set forth in claim 1, wherein the amine (C) is a substituted aromatic amine represented by the following general formula:

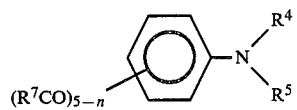

wherein R$^4$ stands for a hydrogen atom or an alkyl group, R$^5$ stands for a hydrogen atom, an alkyl group,, a hydroxyalkyl group or an aryl group, R$^7$ stands for a hydrogen atom, an alkyl group, a hydroxyl group, an alkoxyl group, a hydroxyalkyl group, an aryl group or a group —NR$^8$R$^9$ in which R$^8$ and R$^9$ stand for a hydrogen atom or an alkyl group, and n is an integer of from 0 to 4.

4. A composition as set forth in claim 3, wherein the substituted aromatic amine is 4-dimethylaminobenzaldehyde, 4-dimethylaminobenzoic acid or methyl 4-dimethylaminobenzoate.

5. A composition as set forth in claim 1, wherein the amine (c) is a substituted aromatic amine in which R$^6$ is a cyano group.

6. A composition as set forth in claim 5, wherein the substituted aromatic amine is N,N-dimethyl-p-cyanoaniline or N,N-diethyl-p-cyanoaniline.

7. A composition as set forth in claim 1, wherein the radical-polymerizable monomer is a monomer having at least one acryloyl or methacryloyl group.

8. A composition as set forth in claim 1, wherein the radical-polymerizable monomer is a combination of (i) an ester monomer of an aliphatic alcohol or aliphatic polyol with methacrylic acid and (ii) at least one monomer selected from the group consisting of an ester monomer of a polyol having a bisphenol skeleton or dihydric phenol skeleton with methacrylic acid and a methacryloyloxyl group-containing aromatic polycarboxylic acid or its anhydride.

9. A composition as set forth in claim 8, wherein the monomers (i) and (ii) are present at a (i)/(ii) weight ratio of from 5/95 to 95/5.

10. A composition as set forth in claim 1, wherein the α-ketocarbonyl compound (b) is an α-diketone.

11. A composition as set forth in claim 1, wherein the α-ketocarbonyl compound (b) is benzil or camphorquinone.

12. A composition as set forth in claim 1, wherein the α-ketocarbonyl compound (b) is present in an amount of 0.01 to 15 parts by weight per 100 parts by weight of the radical-polymerizable monomer (a) and the amine (c) is present in an amount of 0.01 to 15 parts by weight per 100 parts by weight of the radical-polymerizable monomer (a).

13. A dental treatment material comprising a composition as set forth in claim 1.

* * * * *